United States Patent [19]
Umezawa et al.

[11] 4,125,706
[45] Nov. 14, 1978

[54] NOVEL PROCESS FOR THE PREPARATION OF 1-N-(ALPHA-SUBSTITUTED-OMEGA-AMINOACYL)-3'-DEOXYRIBOSTAMYCIN

[75] Inventors: Hamao Umezawa; Sumio Umezawa, both of Tokyo; Tsutomu Tsuchiya, Yokohama, all of Japan

[73] Assignee: Zaidan Hojin Biseibutsu Kagaku Kenkyu Kai, Tokyo, Japan

[21] Appl. No.: 676,792

[22] Filed: Apr. 14, 1976

[30] Foreign Application Priority Data

Apr. 24, 1975 [JP] Japan .................................. 50-49106

[51] Int. Cl.² ............................................ C07H 15/20
[52] U.S. Cl. ...................................... 536/17; 536/10; 536/12
[58] Field of Search .................................... 536/10, 17

[56] References Cited

U.S. PATENT DOCUMENTS

| 3,929,762 | 12/1975 | Umezawa et al. | 536/10 |
| 3,960,833 | 6/1976 | Naito et al. | 536/17 |
| 4,003,922 | 1/1977 | Kavadias et al. | 536/17 |

Primary Examiner—Johnnie R. Brown
Attorney, Agent, or Firm—Brady, O'Boyle & Gates

[57] ABSTRACT

A 1-N-(α-substituted-ω-aminoacyl)-3'-deoxyribostamycin, which is a useful antibiotic active against various drug-resistant bacteria, can be prepared advantageously by a process starting from a protected derivative of ribostamycin in the form of 1,6-carbamate and comprising the 3'-deoxygenation, the splitting of the carbamate linkage and the 1-acylation.

7 Claims, No Drawings

NOVEL PROCESS FOR THE PREPARATION OF 1-N-(ALPHA-SUBSTITUTED-OMEGA-AMINOACYL)-3'-DEOXYRIBOSTAMYCIN

The present invention relates to a novel process for the preparation of a 1-N-(α-substituted-ω-aminoacyl)-3'-deoxyribostamycin.

We have been engaged in research and development of antibiotics active against drug-resistant bacteria including *Staphylococcus aureus* and *Pseudomonas aeruginosa*. As a result of further studies based on our discovery concerning the mechanism of resistance of such drug-resistant bacteria isolated from patients, we have synthesized various aminoglycosidic antibiotic derivatives including 3',4'-dideoxyribostamycin (Journal of Antibiotics, 25, 613 (1972) 3'-deoxykanamycin A (U.S. Pat. No. 3,929,761), 3',4'-dideoxykanamycin B U.S. Pat. No. 3,753,973) and 3'-deoxyribostamycin U.K. Pat. No. 1,426,910).

On the other habd, since the discovery of the butirosins A and B, hand, is, 1-N-((S)-α-hydroxy-γ-amino-n-butyryl)-5-O-β-D-xylofuranosyl- and -ribofuranosyl-neamine which are obtained by fermentative technique from natural origins (Tetrahedron Letters, 28, 2617–2620 (1971), it has been estimated that when the (s)-α-hydroxy-γ-aminobutyric acid moiety which is linked as side chain through the 1-amino group of butirosins is condensed with the 1-amino group of a basic aminoglycosidic antibiotic, then the resulting condensation product may gain an antibacterial activity against a variety of drug-resistant bacteria.

In view of the above, we have synthesized 1-N-(α-hydroxy-ωaminobutyryl)-3'-deoxyribostamycin, namely 3'-deoxybutyrosin B (U.K. Pat. No. 1,426,908 and DT-OS No. 2350169).

An object of the present invention is to provide a novel process for preparing a 1-N-(α-hydroxy-ω-aminoacyl)-3'-deoxyribostamycin from ribostamycin in a higher yield and by way of shortened steps.

According to the process of U.K. Pat. No. 1,426,908, which starts from 3'-deoxyribostamycin, the latter is reacted with benzyl-para-nitrophenyl carbonate to protect the 6'-amino group of the ribostamycin and the 6'-N-protected derivative is then reacted with (S)-α-hydroxy-γ-N-phthalimidobutyric acid to effect the 1-N-acylation, followed by removing the protecting group to produce 1-N-((S)-α-hydroxy-γ-aminobutyryl)-3'-deoxyribostamycin. This process starting from 3'-deoxyribostamycin is not fully advantageous since it necessitates the intermediate step of isolating the 3'-deoxyribostamycin in the course of the process. An efficiency of the process may not be satisfactory since this process involves that not only the 1-amino group which is desirable to be acylated, but also the 3- and 2'-amino groups which are not desirable to be acylated can actually be acylated with inevitable by formation of undesirable mixed acylation product.

We have found that a new type reaction occurs between the 1-amino group in the deoxystoreptamine moiety of ribostamycin and the 6-hydroxy group thereof to form the cyclic 1,6-carbamate linkage (Journal of Antibiotics, 25, No. 12, 741–742 (1972). We have now found that by virtue of said new type reaction a 1-N-(α-substituted-ω-aminoacyl)-3'-deoxyribostamycin can be prepared more advantageously according to a process in which the reactive 1-amino and 6-hydroxy groups of ribostamycin are protected by the conversion into the form of the cyclic 1,6-carbamate and the remaining amino groups are protected in a conventional manner, whereupon the resulting protected derivative of ribostamycin is converted into the 3'-deoxy compound (i.e. 3'-deoxygenated), then the 1,6-carbamate linkage is splitted or ring-fissioned to regenerate selectively the free 1-amino group which is subsequently acylated with the α-substituted-ω-amino acid. Alternatively, following the protection steps, the 1,6-carbamate linkage may be first splitted, then the regenerated free 1-amino group is acylated and the resultant acylation product is converted into the 3'-deoxy compound. In further alternative way, the splitting of the 1,6-carbamate linkage and the 1-N-acylation may be carried out during the course of the conversion into the 3'-deoxy compound (i.e. 3'-deoxygenation).

The new process of the present invention, in which the 1-amino group having been selectively regenerated in the unblocked state is selectively acylated and in the course of which the formation and isolation of 3'-deoxyribostamycin is not involved, is commercially advantageous in terms of improved yield and reduced number of the reaction steps.

Accordingly, in a first aspect of the present invention, there is provided a process for the preparation of a 1-N-(α-substituted-ω-aminoacyl)-3'-deoxyribostamycin of the general formula

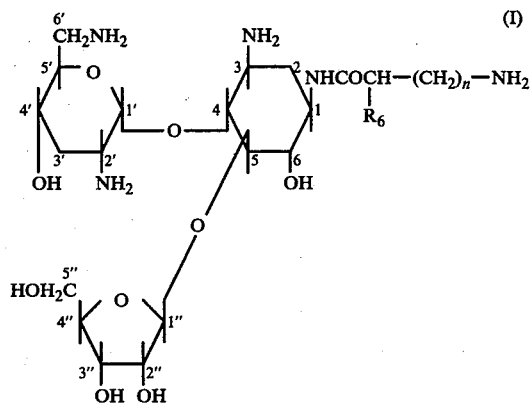

wherein $R_6$ represents —OH, —NH$_2$ or —NHR$_{10}$ group in which R$_{10}$ represents an acyl group and $n$ is an integer of 1 to 4, which comprises the steps of: reacting a compound of the formula:

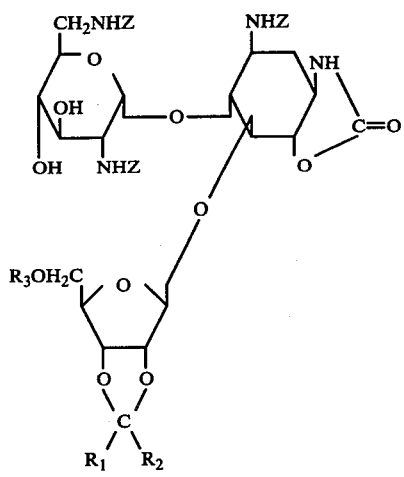 (II)

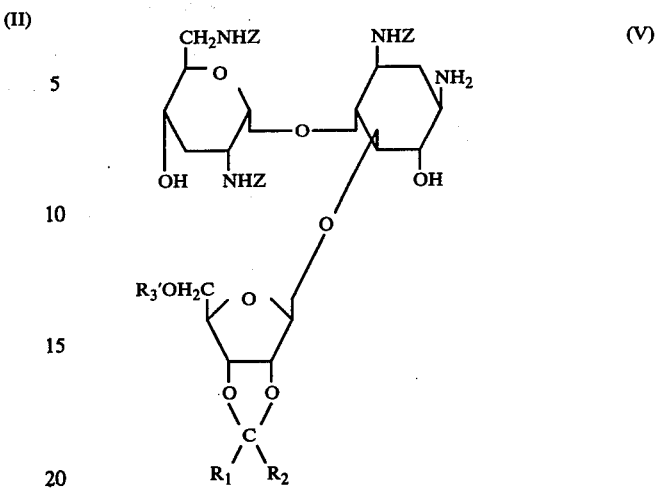 (V)

wherein each of Z represents an amino-protecting group of the formula —$COOR_4$ in which $R_4$ represents an alkyl, aryl or aralkyl group, $R_1$ and $R_2$ which may be the same or different, each represents hydrogen atom or an alkyl or aryl group or $R_1$ and $R_2$ taken together with the adjacent carbon atom form a cycloalkylidene or tetrahydropyranyl group and $R_3$ represents an acyl, aroyl, hemiacetal, hemiketal, alkoxycarbonyl or aralkoxycarbonyl group, with a sulfonylating compound of the formula:

 (III)

wherein $R_5$ represents an alkyl, aryl or aralkyl group and X represents a halogen atom or —$OSO_2R_5$ group, to produce a sulfonyl compound of the formula:

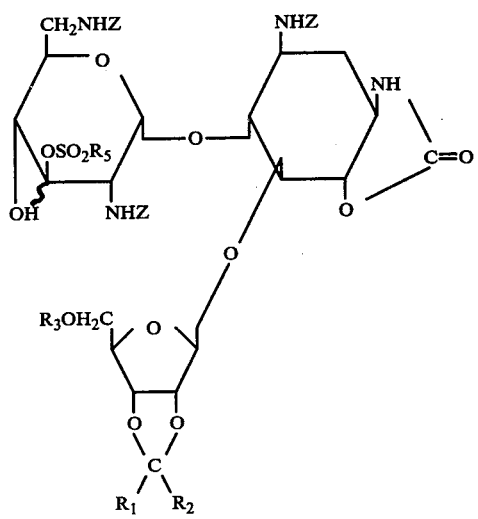 (IV)

wherein Z, $R_1$, $R_2$, $R_3$ and $R_5$ are as defined above; reacting said sulfonyl compound with a halogenating compound to halogenate the 3'-position of the sulfonyl compound; subjecting the 3'-halogenated compound to reduction and then to hydrolysis to produce a compound of the formula:

wherein Z, $R_1$ and $R_2$ are as defined above and $R_3'$ represents hydrogen atom or has the same meaming as $R_3$, interacting the compound of the formula (V) with an acylating compound of the formula:

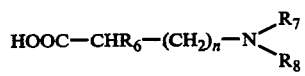 (VI)

or

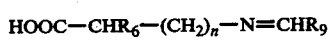 (VII)

wherein $R_6$ and $n$ are as defined above, $R_7$ and $R_8$ each represents hydrogen atom or an acyl, alkyloxycarbonyl, aralkyloxycarbonyl or aryloxycarbonyl group and $R_9$ represents hydrogen atom or an alkyl or aryl group, or with a functional derivative of the carboxylic acid compound to acylate the 1-amino group of the compound (V); and then removing the remaining amino- and hydroxyl-protecting groups from the acylation product in a conventional manner.

In a second aspect of the invention, there is provided a process for the preparation of a compound of the general formula (I) as above, which comprises the steps of: reacting a compound of the formula (II) as above with a sulfonylating compound of the formula (III) as above to produce a sulfonyl compound of the formula (IV) as above; reacting said sulfonyl compound with a halogenating compound to halogenate the 3'-position of the sulfonyl compound; hydrolysing the 3'-halogenated compound into a compound of the formula:

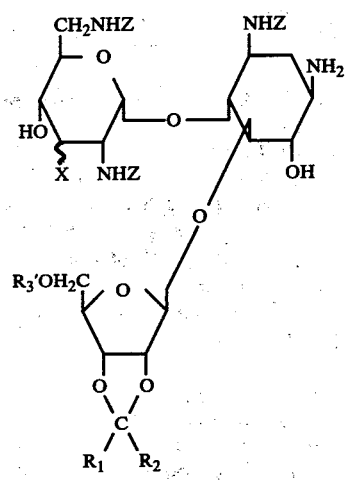

(IV')

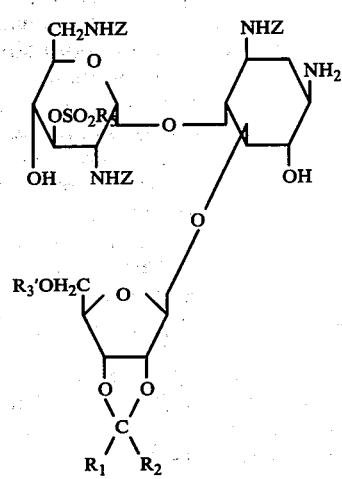

(V')

wherein X represents a halogen atom and Z, $R_1$ and $R_2$ are as defined above; interacting the compound of the formula (IV') with an acylating compound of the formula (VI) or (VII) as above or with a functional derivative thereof to acylate the 1-amino group of the compound (IV'); removing the remaining amino- and hydroxyl-protecting groups from the acylation product in a conventional manner to produce a compound of the formula:

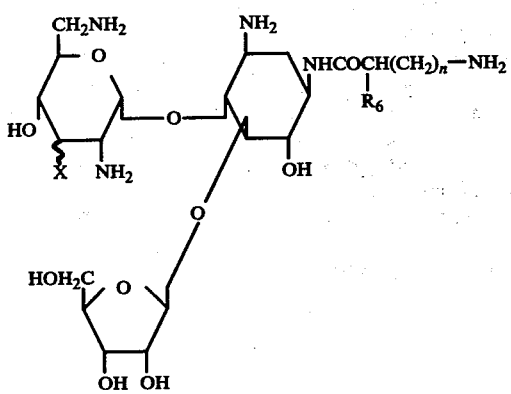

(I')

wherein X, $R_6$ and n are as defined above; and then eliminating the 3'-halo group X from the compound of the formula (I') by the reduction thereof.

In a third aspect of the invention, there is provided a process for the preparation of a compound of the general formula (I) as above, which comprises the steps of: reacting a compound of the formula (II) as above with a sulfonylating compound of the formula (III) as above to produce a sulfonyl compound of the formula (IV) as above; treating said sulfonyl compound under alkaline conditions to split the 1,6-carbamate linkage, whereby there is produced a compound of the formula:

wherein Z, $R_1$, $R_2$ and $R_5$ are as defined above and $R_3'$ represents hydrogen atom or has the same meaning as $R_3$; interacting the compound of the formula (V') with an acylating compound of the formula (VI) or (VII) as above or with a functional derivative thereof to acylate the 1-amino group of the compound (V'); reacting the acylation product with a halogenating compound to halogenate the 3'-position of the acylation product, followed by the reduction of the 3'-halo group; and then removing the remaining amino- and hydroxyl-protecting groups from the resultant product in a conventional manner.

In a fourth aspect of the invention, there is provided a process for the preparation of a compound of the general formula (I) as above, which comprises the steps of: reacting a compound of the formula (II) as above with a sulfonylating compound of the formula (III) as above to produce a sulfonyl compound of the formula (IV) as above; treating said sulfonyl compound under alkaline conditions to split the 1,6-carbamate linkage, leading to the production of a compound of the formula (V') as above; interacting the compound of the formula (V') with an acylating compound of the formula (VI) or (VII) as above or with a functional derivative thereof to acylate the 1-amino group of the compound (V'); reacting the acylation product with a halogenating compound to halogenate the 3'-position of the acylation product; removing the remaining amino- and hydroxyl-protecting groups from the halogenated compound to produce a compound of the formula (I') as above; and then eliminating the 3'-halo group X from the compound of the formula (I') by the reduction thereof.

According to the first aspect of the invention, a protected derivative of ribostamycin-1,6-carbamate having the above formula (II) is reacted with a sulfonylating compound of the above formula (III) whereby the 3'-hydroxyl group is sulfonylated to produce the sulfonyl compound of the above formula (IV).

The sulfonylation is usually carried out in a solvent inert to the reaction, which may include pyridine, dioxane and methylene chloride. Among these, anhydrous pyridine is preferred. The reaction temperature is suitably in the range 10° to 50° C.

Suitable examples of groups $R_1$ and $R_2$ in the formula (II) are hydrogen, an alkyl group containing 1 to 4 carbon atoms such as methyl, ethyl, propyl, isopropyl or butyl group and an aryl group such as phenyl, methylphenyl or methoxyphenyl group. When $R_1$ and $R_2$ form a cycloalkylidene group together with the adjacent carbon atom, it may be suitably one containing 5 to 7 carbon atoms, for example, cyclopentylidene, cyclohexylidene or cycloheptylidene group.

Suitable examples of group $R_3$ include an acyl group such as acetyl, propionyl or butyryl, an aroyl group such as benzoyl, para-chlorobenzoyl or para-nitrobenzoyl, a hemiacetal or hemiketal group such as tetrahydropyranyl or 1-methoxycyclohexyl, an alkoxycarbonyl group such as ethoxycarbonyl, t-butoxycarbonyl or t-amyloxycarbonyl and an aralkoxycarbonyl group such as benzyloxycarbonyl, para-methoxybenzyloxycarbonyl, para-ethoxybenzyloxycarbonyl or para-chlorobenzyloxycarbonyl, Examples of group Z include an alkoxycarbonyl group, particularly, containing 1 to 4 carbon atoms, for example, methoxy-, ethoxy-, propoxy-, isopropoxy- and butoxycarbonyl, an aryloxycarbonyl group, for example, phenoxy- and para-nitrophenoxycarbonyl; an aralkoxycarbonyl group, for example, benzyloxy-, para-methoxybenzyloxy-, para-ethoxybenzyloxy-, para-chlorobenzyloxy- and para-nitrobenzyloxycarbonyl.

Examples of the sulfonylating compound (III) for present use include an alkylsulfonyl halide such as methylsulfonyl chloride, methylsulfonyl bromide, ethylsulfonyl chloride, propylsulfonyl chloride and butylsulfonyl chloride, an aralkylsulfonyl halide such as benzylsulfonyl chloride and an arylsulfonyl halide such as para-toluene-sulfonyl chloride, ortho-nitrobenzene-sulfonyl chloride, para-nitrobenzene-sulfonyl chloride and 2-naphthalene-sulfonyl chloride. Where X represents a group $-OSO_2R_5$, the sulfonylating compound is a sulfonic anhydride including methylsulfonic and toluenesulfonic anhydride.

The 3'-sulfonyl compound of the formula (IV) thus obtained is then reacted with a halogenating compound to produce the 3'-halogenated derivative. A solvent in which the reaction may be carried out includes dimethylformamide, dioxane, tetrahydrofuran, ethyleneglycol dimethyl ether, dimethylacetamide, propyleneglycol dimethyl ether and acetonitril. The halogenating compound to be used may include sodium iodide, potassium iodide, lithium bromide and lithium chloride.

The 3'-halogenated compound obtained is then reduced to produce the 3'-deoxy compound. The reduction is usually carried out in a solvent including dioxane, tetrahydrofuran, methylene chloride, dimethylformamide, acetone, methanol, ethanol and isopropanol, which may be anhydrous or hydrous. The reduction may be carried out with hydrogen gas using as a catalyst Raney nickel, palladium-carbon, palladium-barium carbonate, iron, copper, platinum oxide, rhodium and cobalt alone or in combination. The reduction with hydrogen may be effected at a temperature of $-20°$ to $120°$ C, preferably in the range from room temperature to $100°$ C and under atmospheric pressure or higher, e.g. 1 to 50 kg/cm$^2$. The reaction may be promoted by the addition of a base such as triethylamine or potassium hydroxide.

The 3'-deoxy compound produced in this way is then subjected to hydrolysis with a basic reagent such as sodium hydroxide, barium hydroxide or sodium carbonate so as to produce the compound of the above formula (V) in which only the 1-amino group is in free form and the protecting groups for the other amino groups remain as they are.

On this occasion, the protecting group $R_3$ for the 5"-hydroxyl group may be possibly removed. However, the possible removal in no way affects the subsequent reactions.

The resultant compound of the formula (IV) is reacted with an acylating agent of the formula (VI) or (VII) or a functional equivalent thereof to effect the α-substituted -ω-aminoacylation of the 1-amino group.

A solvent which may be used for the acylation includes water, tetrahydrofuran, dioxane, ethyleneglycol, dimethylether, dimethylformamide, dimethylacetamide and propyleneglycol dimethyl ether and a mixture thereof. A mixed solvent of water and tetrahydrofuran is preferred. The reaction temperature may be below $50°$ C, most preferably below $25°$ C. The functional derivative of the acylating compound (VI) or (VI) may include acid halides, acid azides, active esters and mixed acid anhydrides.

The acylating compound for present use may be in racemic or optically active form, although it is preferred to use a compound of L-form in view of antibacterial activity of the final compound, for example, in case of α-hydroxy-γ-aminobutyric acid ($n=2$) and α-hydroxy-δ-aminovaleric acid ($n=3$).

From the acylation product thus obtained are removed the protecting groups Z

$R_3$, $R_7$, $R_8$ and $R_9$. The group Z may be removed in a conventional manner, for example, by treating with an acid such as acetic acid or a base such as sodium hydroxide, barium hydroxide, sodium carbonate, sodium azide and liquid ammonia or by reduction decomposition with hydrogen over a catalyst selected from palladium, platinum, Raney nickel, rhodium, ruthenium and nickel. In practice, the removal of the protecting groups by the reduction may conveniently be effected in a solvent of water or a water-miscible organic solvent selected from dioxane, tetrahydrofuran, ethyleneglycol dimethyl ether and propyleneglycol dimethyl ether. The conditions to be generally employed for this reduction are hydrogen pressure of 1 to 5 atoms, reaction temperature of $0°$ to $100°$ C and reaction time of 0.5 to 48 hours.

The protecting group

may be conveniently removed by dissolving the acylation product in a 0.5 to 2N solution of an inorganic acid such as hydrochloric or sulfuric acid or an organic acid such as acetic or propionic acid and heating the solution to a temperature up to $100°$ C or by reductive decomposition as mentioned above. The protecting group $R_3$ may be removed by treating with an acid or a base. The groups $R_7$, $R_8$ and $R_9$ may be simultaneously removed by any method as already described.

In such a way, there can be prepared the final compound of the above formula (I), 1-N-(α-substituted-ω-aminoacyl)-3'-deoxyribostamycin.

According to the second aspect of the present invention, the 3'-halogenated derivative of the compound (III) obtained in the process according to the first aspect is then hydrolysed with a base, for example, sodium hydroxide, barium hydroxide, sodium carbonate and the like to produce the compound of the above formula (IV') in which the 1-amino group is in free form. Subsequently, the compound (IV') is subjected to the acylation and the removal of the protecting groups to produce the compound of the above formula (I') which is then reduced to remove the 3'-halo group, these steps being carried out in the same manner and under the same conditions as in the process according to the first aspect. Thereby the final compound of the formula (I) is prepared.

According to the third aspect of the invention, the sulfonyl compound of the formula (III) is treated in a solution of barium hydroxide, sodium carbonate, methanolic ammonia and the like to split the 1,6-carbamate linkage, resulting in the production of the compound having the formula (V'). The treatment is followed by the sequent steps, the acylation, the 3'-halogenation, the reduction and the removal of the protecting groups, as mentioned for the first aspect of the invention, to produce the final compound of the formula (I).

According to the fourth aspect of the present invention, the 3'-halogenated compound obtained in the process according to the third aspect is freed from the protecting groups, followed by the reduction to remove the 3'-halo group, as described hereinbefore.

The final compound of the formula (I) thus prepared may be purified by column chromatography using a cation-exchange resin, for example, Amberlite IRC 50 and CM-Sephadex.

The compound of the formula (I) has a low toxicity and exhibits a high antibacterial activity against various drug-resistant strains, including Pseudomonas aeruginosa and Staphylococcus aureus.

The following Table 1 shows antibacterial spectra, in terms of minimum inhibitory concentration (MIC, mcg/ml), of 1-N-((S)-α-hydroxy-ω-aminobutryl)-3'-deoxyribostamycin (3'-deoxybutirosin B), 1-N-((S)-β-amino-α-hydroxypropionyl)-3'-deoxyribostamycin and 1-N-((RS)-β-amino-α-hydroxypropionyl)-3'-deoxyribostamycin which are prepared by the present process, together with that of butirosin B by way of comparison.

active against various gram-positive and gram-negative bacteria, including butirosin-resistant strains.

The compounds of the formula (II) to be used as starting material in the process of the present invention are all novel in themselves. They may be prepared, for example, in the following manner:

Tetra-N-benzyloxycarbonyl-3',4':2",3"-di-O-cyclohexylidene-5"-O-(1-methoxycyclohexyl)-ribostamycin (made by the method described in "Bull. Chem. Soc." Japan, 46, 3210 (1973) is dissolved in a mixture of acetic acid and acetone to remove the 1-methoxycyclohexyl group at the 5"-position of said ribostamycin. The reaction product obtained is dissolved in anhydrous dimethylformamide and then interacted with 50% sodium hydride in dimethylformamide to produce tri-N-benzyloxycarbonyl-3',4':2",3"-O-cyclohexylideneribostamycin 1,6-carbamate (Journal of Antibiotics, 25, No. 12, 741 (1972). The latter is subjected to acetylation with acetic anhydride in anhydrous pyridine and then treated with acetic acid to remove selectively the 3',4'-cyclohexylidene group, yielding 5"-O-acetyl-tri-N-benzyloxycarbonyl-2",3"-O-cyclohexylideneribostamycin 1,6-carbamate which is one of the compounds having the formula (II).

The present invention is further illustrated by, but not limited to, the following Examples.

EXAMPLE 1

Preparation of 1-N-((S)-γ-amino-α-hydroxybutyryl)-3'-deoxyribostamycin (namely, 3'-deoxybutirosin B)

(a)

5"-O-acetyl-tri-N-benzyloxycarbonyl-2",3"-O-cyclohexylidene-3'-O-tosylribostamycin 1,6-carbamate 1.77 g of 5'-O-acetyl-tri-N-benzyloxycarbonyl-2",3"-O-cyclohexylideneribostamycin 1,6-carbamate was dissolved in anhydrous pyridine, to which was then added 1.9 g of p-toluenesulfonyl chloride, and the mixture was allowed to stand overnight at 37° C. Thereafter, the solvent was distilled off and the residue was purified by column chromatography using silica gel and benzene- Table 1

| Test organisms | Butirosin B | 3'-deoxy-butirosin B | 1-N-((S)-β-amino-α-hydroxypropionyl)-3'-deoxyribostamycin | 1-N-((RS)-β-amino-α-hydroxypropionyl)-3'-deoxyribostamycin |
|---|---|---|---|---|
| Staphylococcus aureus FDA 209P | 1.56 | 0.39 | 1.56 | 3.12 |
| Sarcina lutea PCI 1001 | 25 | 25 | 25 | 25 |
| Bacillus subtilis B-558 | 0.2 | <0.2 | 0.78 | 1.56 |
| Klebsiella pneumoniae PCI 602 | 0.39 | 0.39 | 1.56 | 1.56 |
| Klebsiella pneumoniae 22 #3038 | >100 | 0.78 | 0.78 | 1.56 |
| Salmonella typhosa T-63 | 0.39 | 0.39 | 0.78 | 0.78 |
| Escherichia coli NIHJ | 0.78 | 0.78 | 1.56 | 1.56 |
| Escherichia coli K-12 | 0.39 | 0.2 | 0.39 | 0.78 |
| Escherichia coli K-12 ML1629 | 0.78 | 0.39 | 1.56 | 1.56 |
| Escherichia coli K-12 ML1630 | 3.12 | 1.56 | 1.56 | 3.12 |
| Escherichia coli K-12 ML1410 | 0.78 | 0.78 | 1.56 | 3.12 |
| Escherichia coli K-12 ML1410 R81 | 3.12 | 0.78 | 0.78 | 6.25 |
| Escherichia coli K-12 LA290 R55 | 0.78 | 0.78 | 0.78 | 1.56 |
| Escherichia coli K-12 LA290 R56 | 0.39 | 0.39 | 0.78 | 1.56 |
| Escherichia coli K-12 LA290 R64 | 0.39 | 0.2 | 0.78 | 0.78 |
| Escherichia coli K-12 W677 | 0.78 | 0.39 | 0.78 | 1.56 |
| Escherichia coli K-12 JR66/W677 | >100 | 1.56 | 3.12 | 3.12 |
| Pseudomonas aeruginosa A3 | 6.25 | 1.56 | 1.56 | 6.25 |
| Pseudomonas aeruginosa No.12 | 25 | 6.25 | 6.25 | 12.5 |
| Pseudomonas aeruginosa GN315 | >100 | >100 | >100 | >100 |
| Pseudomonas aeruginosa TI-13 | 12.5 | 3.12 | 3.12 | 6.25 |
| Pseudomonas aeruginosa 99 | 100 | 12.5 | 12.5 | 12.5 |
| Proteus rettgeri GN311 | 6.25 | 3.12 | 6.25 | 6.25 |
| Proteus rettgeri GN466 | 3.12 | 0.78 | 1.56 | 3.12 |
| Mycobacterium smegmatis 607 | 0.39 | 10.2 | 0.39 | 0.39 |

As is seen from Table 1, the three compounds prepared by the present process are valuable antibiotics ethyl acetate (1:1) as eluent to give a solid. 1.55 g (76%); $[\alpha]_D^{20} = +13°$ (c = 1.7 in chloroform).

Analysis: Found: C, 59.30; H, 5.78; N, 4.72; S, 2.66%. Calcd. for $C_{57}H_{66}N_4O_{20}S$: C, 59.06; H, 5.74; N, 4.83; S, 2.77%.

(b)
5''-O-acetyl-tri-N-benzyloxycarbonyl-2'',3''-O-cyclohexylidene-3''-O-(o-nitrobenzenesulfonyl)-ribostamycin 1,6-carbamate The replacement of p-toluenesulfonyl chloride by O-nitrobenzenesulfonyl chloride in the process of Example 1(a) gave the titled compound in 55% yield. M.p. 114°–116° C. $[\alpha]_D^{14} = +6.5°$ (c = 2.3 in chloroform).

Analysis: Found: C, 56.25; H, 5.40; N, 5.75; S, 2.88%. Calcd. for $C_{56}H_{63}N_5O_{22}S$: C, 56.51; H, 5.34; N, 5.88; S, 2.69%.

(c)
5''-O-acetyl-tri-N-benzyloxycarbonyl-2'',3''-O-cyclohexylidene-3'-iodoribostamycin 1,6-carbamate 0.95 g of the product obtained in Example 1(b) was dissolved in 20 ml of dimethylformamide, to which was added 9.5 g of sodium iodide, and the mixture was heated at 100° C for 1.5 hours. A great volume of chloroform was added to the reaction solution and the resultant solution filtered and then washed with brine. The solvent was removed from the chloroform solution by distillation to give a solid residue, which was purified by column chromatography using silica gel and benzene-ethyl acetate (1:1) as eluate. Yield 0.49 g (55%); $[\alpha]_D^{14} = +4.6°$ (c = 2.7 in chloroform).

Analysis: Found: C, 54.23; H, 5.49; N, 5.02; I, 11.05%. Calcd. for $C_{50}H_{59}N_4O_{17}I$: C, 53.86; H, 5.34; N, 5.03; I, 11.38%.

The compound obtained in Example 1(a) was treated as above to give the titled compound in 47% yield.

(d)
5''-O-acetyl-tri-N-benzyloxycarbonyl-2'',3''-O-cyclohexylidene-3'-deoxyribostamycin 1,6-carbamate 1.0 g of the product obtained in Example 1(b) was dissolved in 25 ml of dimethylformamide, to which was added 10 g of lithium chloride and the mixture heated at 100° C for 1.5 hours. The reaction mixture was then treated as in Example 1(c) to give 0.45 g of the desired compound. $[\alpha]_D^{18} = +4.3°$ (c = 1 in chloroform).

Analysis: Found: C, 58.59; H, 5.72; N, 5.30; Cl, 3.34%. Calcd. for $C_{50}H_{59}N_4O_{17}Cl$: C, 58.67; H, 5.81; N, 5.47; Cl, 3.47%.

(e)
5''O-acetyl-tri-N-benzyloxycarbonyl-2'',3''O-cyclohexylidene3'-deoxyribostamycin 1,6-carbamate 310 mg of the product obtained in Example 1(c) was dissolved in 9 ml of dioxane, to which was added 50 mg of triethylamine. The mixture was subjected to reduction with hydrogen gas flow in the pressure of Raney nickel and then treated in a conventional manner. Yield 170 mg (62%); $[\alpha]_D^{13} = +5°$ (c = 1 in chloroform); M.p. = 97°–99° C.

Analysis: Found: C, 60.35; H, 6.20; N, 5.52%. Calcd. for $C_{50}H_{60}N_4O_{17}$: C, 60.72; H, 6.11; N, 5.66%.

(f) 3,2',6'-Tri-N-benzyloxycarbonyl-2'',3''-O-cyclohexylidene-3'-deoxyribostamycin 1.56 mg of the product obtained in Example 1(e) was dissolved in 3 ml of dioxane, to which was added 2.4 ml of 0.2N aqueous barium hydroxide solution and the mixture heated at 60° C for 1 hour. Gaseous carbon dioxide was blown into the mixture, followed by filtering and the solvent was distilled off to give a solid. Yield 151 mg; $[\alpha]_D^{20} = +12°$ (c = 1 in chloroform).

(g)
3,2',6'-tri-N-benzyloxycarbonyl-1-N-((S)-γ-benzyloxycarbonylamino-2-hydroxybutyryl)-2'',3''-O-cyclohexylidene-3''-deoxyribostamycin 370 mg of the solid product obtained in Example 1(f) was dissolved in 8 ml of tetrahydrofuran, to which was added 40 mg of triethylamine and the mixture cooled with ice. Then, 0.17 g of N-hydroxysuccinimide ester of (S)-γ-benzyloxycarbonylamino-α-hydroxybutyric acid was added thereto, and the resultant mixture allowed to stand with ice-cooling for 1 hour. The solution was concentrated under reduced pressure and the residue dissolved in ethyl acetate, followed by filtering and removal of the solvent under reduced pressure. The residue so obtained was purified by column chromatography using silica gel and chloroform-isopropyl alcohol (10:1 by volume) as eluent. Yield 202 mg; $[\alpha]_D^{18} = +2.5°$ (c = 1 in chloroform); M.p. 102°–106° C.

Analysis: Found: C, 61.11; H, 6.39; N, 6.33%. Calcd. for $C_{59}H_{73}N_5P_{19}$: C, 61.29; H, 6.36; N, 6.06%.

(h)
1-N-((S)-γ-amino-α-hydroxybutyryl)-3'-deoxyribostamycin (namely, 3'-deoxybutirosin B)

178 mg of the product obtained in Example 1(g) was dissolved in 4.3 ml of dioxane, to which was added 1.4 ml of water and the mixture reduced with a catalyst of palladium black. The solution was then filtered and the filtrate concentrated to dryness under reduced pressure. The resultant solid was dissolved in 1N hydrochloric acid, which was brought into reaction at 60° C for 1 hour (for the removal of the cyclohexylidene group). The crude product thus obtained was chromatographically purified by eluting with aqueous ammonia in a column of CM-Sephadex C-25, while the concentration of ammonia in the eluent was progressively increased from 0 to 0.4N. The fractions containing the desired compound were collected, combined together and then concentrated. Yield 34 mg (37%); $[\alpha]_D^{24} = +27°$ (c = 2 in water).

Analysis: Found: C, 43.44; H, 7.26; N, 11.45%. Calcd. for $C_{21}H_{41}N_5O_{11}\cdot H_2CO_3$: C, 43.92; H, 7.20; N, 11.64%.

EXAMPLE 2

Preparation of 1-N-((S)-γ-amino-α-hydroxybutyryl)-3'-deoxyribostamycin (a)
3,2',6'-tri-N-benzyloxycarbonyl-3'-chloro-2'',3''-O-cyclohexylideneribostamycin 140 mg of the compound of Example 1(d) was dissolved in 3 ml of dioxane, to which was added 2.5 ml of 0.2N aqueous barium hydroxide solution and the mixture heated at 60° C for 1 hour. Gaseous carbon dioxide was then brown into the mixture followed by filtering, and the solvent distilled off to give a solid. Yield 123 mg; $[\alpha]_D^{20} = +12°$ (c = 1 in chloroform).

(b)
3,2',6'-tri-N-benzyloxycarbonyl-1-N-((S)-γ-benzyloxycarbonylamino-α-hydroxybutyryl)-3'-chloro-2'',3''-O-cyclohexylideneribostamycin 340 mg of the product obtained in Example 2(a) was dissolved in 8 ml of tetrahydrofuran, to which was added 40 mg of triethylamine and the mixture cooled with ice. 0.18 g of N-hydroxysuccinimide ester of (S)-γ-benzyloxycarbonylamino-α-hydroxybutyric acid was then added and the resultant mixture allowed to stand with ice-cooling for 1 hour. The mixture was subsequently treated as in Example 1(f) to give a solid. Yield 190 mg; $[\alpha]_D^{20} = 3.2°$ (c = 1 in chloroform).

Analysis: Found: C, 59.43; N, 6.00; N, 5.81; Cl, 2077%. Calcd. for $C_{59}H_{72}N_5O_{19}Cl$: C, 59.51; H, 6.10; N, 5.88; Cl, 2.98%.

(c)
1-N-((S)-γ-amino-α-hydroxybutyryl)-3'-chlororibostamycin 160 mg of the product obtained in Example 2(b) was dissolved in 5 ml of dioxane, to which was added 1.5 ml of water, and the mixture was subjected to reduction with a catalyst of palladium black. The same treatment as in Example 1(h) gave 52 mg of the titled compound. $[\alpha]_D^{24} = +24°$ (c = 1 in water).

Analysis: Found: C, 41.30; H, 6.77; N, 10.86; Cl, 5.45%. Calcd. for $C_{21}H_{40}N_5O_{11}Cl.H_2CO_3$: C, 41.54; H, 6.66; N, 11.01; Cl, 5.58%.

(d)
1-N-((S)-γ-amino-α-hydroxybutyryl-3'-deoxyribostamycin 20 mg of the product obtained in Example 2(c) was dissolved in 1 ml of water, to which 3 mg of potassium hydroxide was added, and the mixture was reduced with Raney nickel by the passage of hydrogen gas. Gaseous carbon dioxide was blown into the mixture followed by concentration to dryness to give a crude product. The product was eluted with aqueous ammonia in a column of CM-Sephadex C-25, while the concentration of ammonia in the eluent was gradually increased from 0 to 0.4N. The fraction containing the desired product was collected and concentrated to yield 13 mg of the same compound as that obtained in Example 1(h).

EXAMPLE 3

Preparation of 1-N-((RS)-β-amino-α-hydroxypropionyl)-3'-deoxyribostamycin

(a)
3,2',6'-tri-N-benzyloxycarbonyl-2'',3''-O-cyclohexylidene-3'-O-tosylribostamycin 303 mg of the compound of Example 1(a) was dissolved in 6 ml of dioxane, to which was added 6 ml of 0.2N aqueous barium hydroxide solution and the mixture heated at 60° C for 1 hour. Gaseous carbon dioxide was blown into the mixture followed by filtering and the filtrate concentrated to give a solid. The solid was dissolved in hot dioxane, the solution was filtered and then concentrated to dryness to yield 245 mg of the desired solid product. $[\alpha]_D^{20} = +7°$ (c = 1 in chloroform).

Analysis: Found: C, 59.31; H, 6.23N, 5.00; S, 2.76%. Calcd. for $C_{54}H_{66}N_4O_{18}S$: C, 59.44; N, 6.10; N, 5.13; S, 2.94%.

(b)
3,2',6'-tri-N-benzyloxycarbonyl-1-N-((RS)-β-benzyloxycarbonylamino-α-hydroxypropionyl)-2'',3''-O-cyclohexylidene-3'-O-tosylribostamycin 250 mg of the product obtained in Example 3(a) was dissolved in 5 ml of tetrahydrofuran, to which was added 25 mg of triethylamine and the mixture cooled with ice. 0.12 g of N-hydroxysuccinimide ester of (RS)-β-benzyloxycarbonylamino-α-hydroxypropionic acid was then added and the resultant mixture allowed to stand with ice-cooling for 1 hour. The solution was concentrated under reduced pressure and the residue dissolved in ethyl acetate followed by filtering. The solvent was removed from the filtrate by distillation and the residue purified by column chromatography using silica gel and chloroform-isopropylalcohol (10:1) as eluent. Yield 185 mg, $[\alpha]_D^{18} = +4°$ (c = 1 in chloroform).

Analysis: Found: C, 59.83; H, 6.05; N, 4.13; S, 2.22%. Calcd. for $C_{65}H_{77}N_5O_{22}S$: C, 60.13; H, 5.98; N, 4.32; S, 2.47%.

(c)
3,2',6'-tri-N-benzyloxycarbonyl-1-N-((RS)-β-benzyloxycarbonylamino-α-hydroxypropionyl)-2'',3''-O-cyclohexylidene-3'-iodoribostamycin 0.1 g of the product obtained in Example 3(b) was dissolved in 2 ml of dimethylformamide, to which was added 1 g of sodium iodide and the mixture heated at 100° C for 1 hour. A great volume of chloroform was added to the reaction solution, which was then filtered and the filtrate washed with saturated brine. The chloroform solution was concentrated to dryness to give a solid, which was purified by column chromatography using silica gel and benzene-ethyl acetate (1:1) as eluent. Yield 0.06 g; $[\alpha]_D^{20} = +5°$ (c = 1 in chloroform).

Analysis: Found: C, 55.11; H, 5.71; N, 5.38; I, 9.96%. Calcd. for $C_{58}H_{70}N_5O_{19}I$: C, 54.93; H, 5.56; N, 5.52; I, 10.01%.

(d)
3,2',6'-tri-N-benzyloxycarbonyl-1-N-((RS)-β-benzyloxycarbonylamino-α-hydroxypropionyl)-3'-chloro-2'',3''-O-cyclohexyldeneribostamycin 105 mg of the product obtained in Example 3(b) was dissolved in 2 ml of dimethylformamide, to which was added 1.2 mg of lithium chloride and the mixture heated at 100° C for 1 hour. The mixture was then treated as in Example 3(c) to give the desired product. Yield 71 mg; $[\alpha]_D^{18} = +4.2°$ (c = 1 in chloroform).

(e)
3,2',6'-tri-N-benzyloxycarbonyl-1-N-((RS-β-benzyloxycarbonylamino-α-hydroxypropionyl)-2'',3''-O-cyclohexylidene-3''-deoxyribostamycin 50 mg of the product obtained in Example 3(c) was dissolved in 2 ml of dioxane, to which was added 10 mg of triethylamine and the mixture subjected to reduction with hydrogen gas flow in the presence of Raney nickel. The subsequent treatment in a conventional manner gave the desired compound. Yield 39 mg; $[\alpha]_D^{15} = +3°$ (c = 1 in chloroform).

Analysis: Found: C, 60.87; H, 6.29, N, 6.03%. Calcd. for $C_{58}H_{71}N_5O_{19}$: C, 60.99; H, 6.27; N, 6.13%.

(f)
1-N-((RS)-β-amino-α-hydroxypropionyl)-3'-deoxyribostamycin 10 mg of the product obtained in Example 3(e) was dissolved in 1 ml of dioxane, to which 0.3 ml of water was added and the mixture subjected to reduction with hydrogen in the presence of a catalyst of palladium black. The subsequent treatment as in Example 1(h) yielded the desired compound. Yield 2.3 mg; $[\alpha]_D^{20} = +38°$ (c = 1 in water).

Analysis: Found: C, 43.23; H, 7.15; N, 11.98%. Calcd. for $C_{20}H_{39}N_5O_{11}\cdot H_2CO_3$: C, 42.92, H, 7.03; N, 11.92%.

EXAMPLE 4

Preparation of 1-N-((S)-β-amino-α-hydroxypropionyl)-3'-deoxyribostamycin

Starting from 300 mg of the compound obtained in Example 3(a), the procedure of Example 3(b) was repeated except that (RS)-β-benzyloxycarbonylamino-α-hydroxypropionic acid was replaced by (S)-β-benzyloxycarbonylamino-α-hydroxypropionic acid. There was thus obtained 3,2',6'-tri-N-benzyloxycarbonyl-1-N-((S)-β-benzyloxycarbonylamino-α-hydroxypropionyl)-2",3"-O-cyclohexylidene-3'-O-tosylribostamycin, which was treated successively as in Examples 3(c), (d) and (e) to yield 26 mg of the titled compound. $[\alpha]_D^{18} = +25°$ (c = 1 in water).

Analysis: Found: C, 43.19; H, 6.88; N, 11.68%. Calcd. for $C_{20}H_{39}N_5O_{11}\cdot H_2CO_3$: C, 42.92; H, 7.03; N, 11.92%.

EXAMPLE 5

Preparation of 1-N-((RS)-β-amino-α-hydroxypropionyl)-3'-chlororibostamycin 52 mg of the compound obtained in Example 3(d) was dissolved in 2 ml of dioxane, to which was added 0.6 ml of water, followed by reduction with hydrogen over a catalyst of palladium black. The subsequent treatment as in Example 1(h) gave 18 mg of the titled compound. $[\alpha]_D^{24} = +35°$ (c = 1 in water).

Analysis: Found: C, 41.58; H, 6.19; N, 10.92; Cl, 5.41%. Calcd. for $C_{20}H_{38}N_5O_{11}Cl\cdot H_2CO_3$: C, 41.67; H, 6.36; N, 11.05; Cl, 5.60%.

Further treatment of the above compound as in Example 2(c) gave 1-N-((RS)-β-amino-α-hydroxypropionyl)-3'-deoxyribostamycin which is the same as that obtained in Example 3(f).

EXAMPLE 6

This Example illustrates the preparation of 5"-O-acetyl-tri-N-benzyloxycarbonyl-2",3"-O-cyclohexylideneribostamycin 1,6-carbamate which is a compound of the formula (II) to be used as starting material in the present invention.

(a)
Tetra-N-benzyloxycarbonyl-3',4':2",3"-di-O-cyclohexylideneribostamycin

Tetra-N-benzyloxycarbonyl-3',4':2",3"-di-O-cyclohexylidene-5"-O-(1-methoxycyclohexyl)-ribostamycin (Bull. Chem. Soc., Japan, 46, 3210 (1973) was dissolved in a mixture of 40% acetic acid/acetone (1:5) by volume), and the resultant mixture allowed to stand at 37° C for 7 hours. The reaction solution was then poured into a mixture of saturated sodium bicarbonate solution and chloroform. The chloroform layer was separated and the solvent distilled off under reduced pressure. The residual solid was purified by column chromatography using silica gel and benzene/ethyl acetate (5:3) as eluent. Yield 63%; $[\alpha]_D^{20} = +23°$ (c = 2 in chloroform).

Analysis: Found: C, 63.51; H, 6.47; N, 4.85%. Calcd. for $C_{61}H_{74}N_4O_{18}$: C, 63.64; H, 6.48; N, 4.87%.

(b)
Tri-N-benzyloxycarbonyl-3',4':2",3"-di-O-cyclohexylideneribostamycin 1,6-carbamate The product obtained in step (a) was dissolved in 11 ml of anhydrous dimethylformamide and the solution ice-cooled. 86 mg of 50% sodium hydride in oil was added to the solution and agitated for an hour, followed by addition of acetic acid. The resultant solution was poured into a mixture of water-chloroform. The chloroform layer was separated and dried over anhydrous sodium sulfate and the solvent was then distilled off to give a solid. Yield 0.59 g (65%). $[\alpha]_D^{20} = +26°$ (c = 2 in chloroform). I.R. spectrometry: 1770 cm$^{-1}$ (due to cyclic carbamate).

Analysis: Found: C, 62.07; H, 6.44; N, 5.50%. Calcd. for $C_{54}H_{66}N_4O_{17}$: C, 62.18; H, 6.38; N, 5.37%.

(c)
5"-O-acetyl-tri-N-benzyloxycarbonyl-2",3"-O-cyclohexylideneribostamycin 1,6-carbamate 2.9 g of the product obtained in step (b) was dissolved in 50 ml of anhydrous pyridine, to which was added acetic anhydride, followed by acetylation (5"-O-acetylation) in a usual manner. The acetylated derivative thus obtained was dissolved in 120 ml of a mixture of 60% acetic acid-acetone (1:1) and heated at 60° C for 1 hour. The solvent was then distilled off to leave a solid, which was triturated with chloroform. The chloroform solution was washed with water, dried over sodium sulfate and the solvent was distilled off to give the titled compound. Yield 2.6 g (93%); $[\alpha]_D^{20} = +11°$ (c = 1.9 in chloroform). M.p. 109°–112° C Analysis: Found: C, 59.59; H, 6.04; N, 5.33%. Calcd. for $C_{50}H_{60}N_4O_{18}$: C, 59.75; H, 6.02; N, 5.57%.

We claim:

1. A process for the preparation of a 1-N-(α-substituted-ω-aminoacyl)-3'-deoxyribostamycin of the general formula:

$$(I)$$

wherein $R_6$ represents —OH and $n$ is an integer of 1 to 4, which comprises the steps of:
   reacting a compound of the formula:

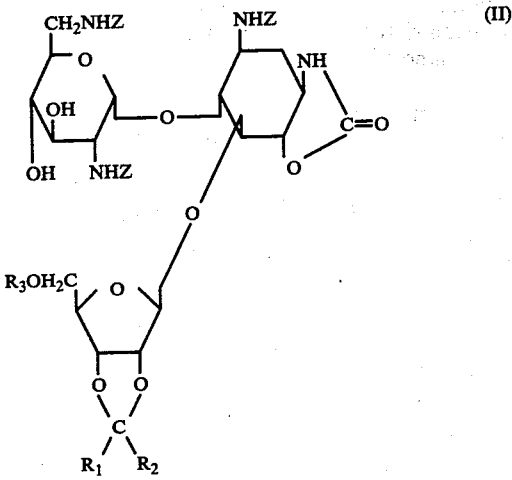

(II)

wherein each of Z represents an amino-protecting group of the formula $-COOR_4$ in which $R_4$ represents an alkyl, aryl or aralkyl group, $R_1$ and $R_2$ which may be the same or different, each represents hydrogen or an alkyl or aryl group or $R_1$ and $R_2$ taken together with the adjacent carbon atom form a cycloalkylidene or tetrahydropyranyl group and $R_3$ represents acetyl, propionyl, butyryl, benzoyl, para-chlorobenzoyl, p-nitrobenzoyl, tetrahydropyranyl, 1-methoxycyclohexyl, ethoxycarbonyl, t-butoxycarbonyl, t-amyloxycarbonyl, benzyloxycarbonyl, p-methoxybenzyloxycarbonyl, p-ethoxybenzyloxycarbonyl or p-chlorobenzyloxycarbonyl, with a sulfonylating compound of the formula:

$R_5SO_2X$      (III)

wherein $R_5$ represents methyl, ethyl, propyl, butyl, benzyl, p-toluyl, o-nitrophenyl, p-nitrophenyl or 2-naphthyl and X represents chlorine or bromine or $-OSO_2R_5$ group, to produce a sulfonyl compound of the formula:

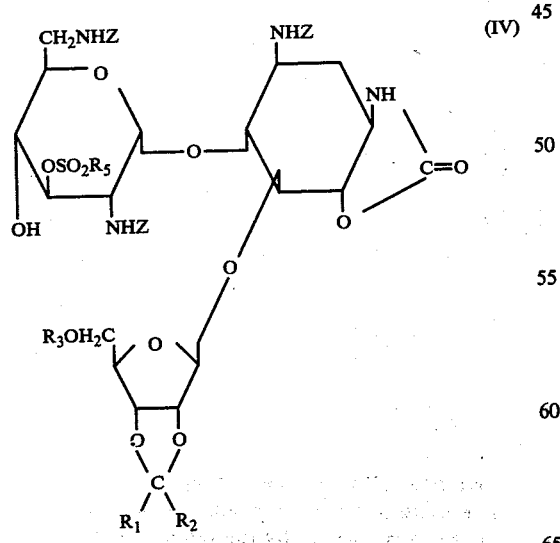

(IV)

wherein Z, $R_1$, $R_2$, $R_3$ and $R_5$ are as defined above; reacting said sulfonyl compound with an appropriate halogenating compound to iodinate, chlorinate or brominate the 3′-position of the sulfonyl compound;

subjecting the 3′-halogenated compound to reduction and then to hydrolysis to produce a compound of the formula:

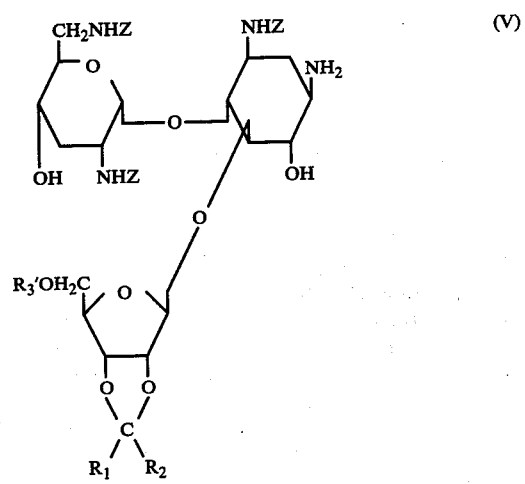

(V)

wherein Z, $R_1$ and $R_2$ are as defined above and $R_3'$ represents hydrogen or has the same meaning as $R_3$;

interacting the compound of the formula (V) with an acylating compound of the formula:

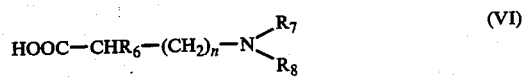

$$HOOC-CHR_6-(CH_2)_n-N\begin{matrix}R_7\\R_8\end{matrix} \quad (VI)$$

or

$$HOOC-CHR_6-(CH_2)_n-N=CHR_9 \quad (VII)$$

wherein $R_6$ and $n$ are as defined above, $R_7$ and $R_8$ each represents hydrogen or an acyl, alkyloxycarbonyl, aralkyloxycarbonyl or aryloxycarbonyl group and $R_9$ represents hydrogen or an alkyl or aryl group, or with a functional derivative of the carboxylic acid compound to acylate the 1-amino group of the compound (V); and then removing the remaining amino- and hydroxyl-protecting groups from the acylation product.

2. A process for the preparation of a compound of the general formula (I) as defined in claim 1, which comprises the steps of:

reaction a compound of the formula:

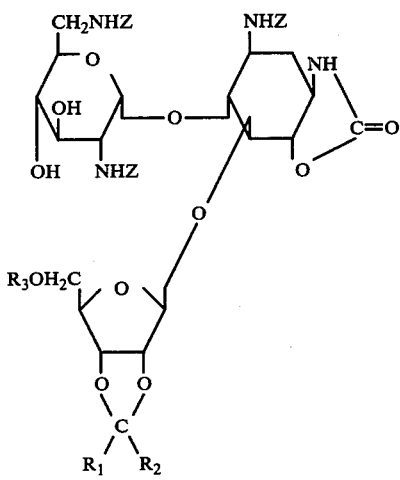 (II)

wherein each of Z represents an amino protecting group of the formula —COOR$_4$ in which R$_4$ represents an alkyl aryl or aralkyl group, R$_1$ and R$_2$ which may be the same or different, each represents hydrogen or an alkyl or aryl group or R$_1$ and R$_2$ taken together with the adjacent carbon atom form a cycloalkylidene or tetrahydropyranyl group and R$_3$ represents acetyl, propionyl, butyryl, benzoyl, para-chlorobenzoyl, p-nitrobenzoyl, tetrahydropyranyl, 1-methoxycyclohexyl, ethoxycarbonyl, t-butoxycarbonyl, t-amyloxycarbonyl, benzyloxycarbonyl, p-methoxybenzyloxycarbonyl, p-ethoxybenzyloxycarbonyl or p-chlorobenzyloxycarbonyl, with a sulfonylating compound of the formula:

 (III)

wherein R$_5$ represents methyl, ethyl, propyl, butyl, benzyl, p-toluyl, o-nitrophenyl, p-nitrophenyl or 2-naphthyl and X represents chlorine or bromine or —OSO$_2$R$_5$ group, to produce a sulfonyl compound of the formula:

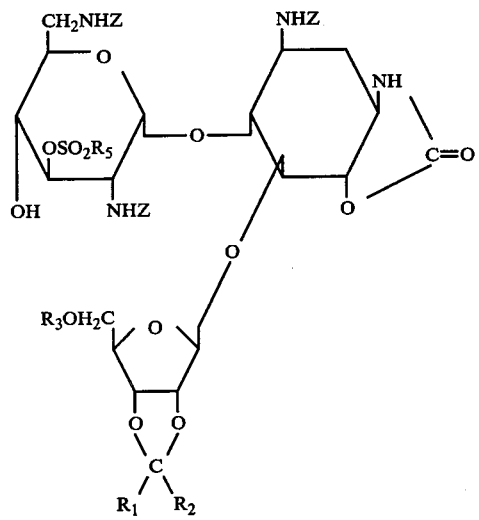 (IV)

wherein Z, R$_1$, R$_2$, R$_3$ and R$_5$ are as defined above; reacting said sulfonyl compound with an appropriate halogenating compound to iodinate, chlorinate or brominate the 3'-position of the sulfonyl compound;

hydrolyzing the 3'-halogenated compound into a compound of the formula:

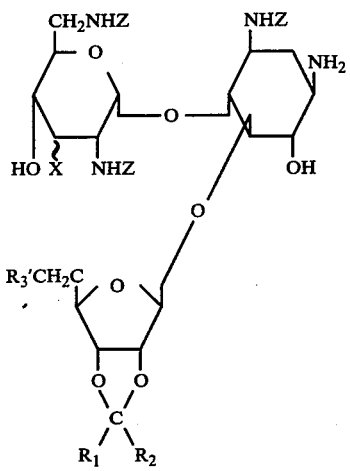 (IV')

wherein X represents a halogen and Z, R$_1$ and R$_2$ are as defined above;

interacting the compound of the formula (IV') with an acylating compound of the formula:

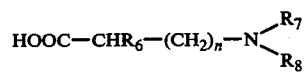 (VI)

or

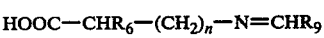 (VII)

wherein R$_6$ represents —OH, n is an integer of 1 to 4, R$_7$ and R$_8$ each represents hydrogen or an acyl, alkyloxycarbonyl, aralkyloxycarbonyl or aryloxycarbonyl group and R$_9$ represents hydrogen or an alkyl or aryl group, or with a functional derivative of the carboxylic acid compound, to acylate the 1-amino group of the compound (IV');

removing the remaining amino- and hydroxyl-protecting groups from the acylation product to produce a compound of the formula:

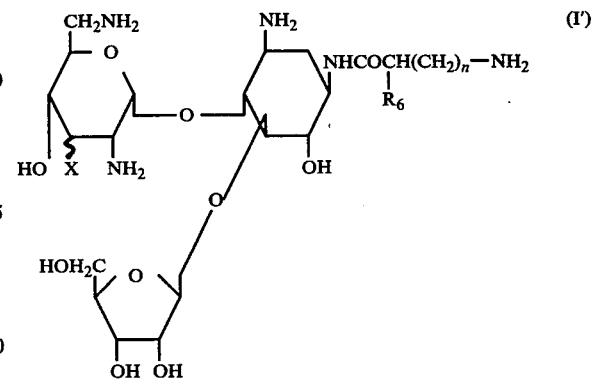 (I')

wherein X, R$_6$ and n are as defined above; and then eliminating the 3'-halo group X from the compound of the formula (I') by the reduction thereof.

3. A process for the preparation of a compound of the general formula (I) as defined in claim 1, which comprises the steps of:

acting a compound of the formula:

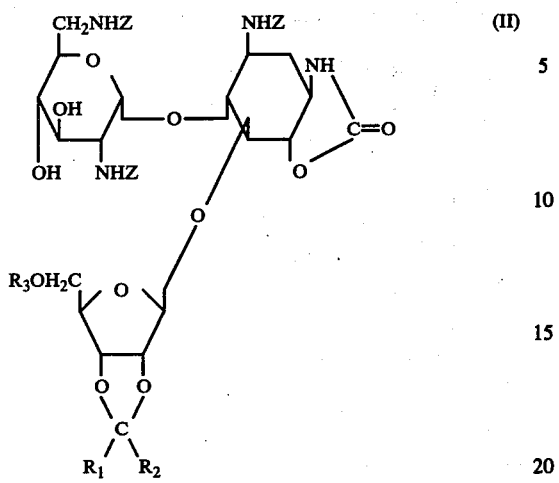

wherein each of Z represents an amino-protecting group of the formula —COOR$_4$ in which R$_4$ represents an alkyl, aryl or aralkyl group, R$_1$ and R$_2$ which may be the same or different, each represents hydrogen or an alkyl or aryl group or R$_1$ and R$_2$ taken together with the adjacent carbon atom form a cycloalkylidene or tetrahydropyranyl group and R$_3$ represents acetyl, propionyl, butyryl, benzoyl, para-chlorobenzoyl, p-nitrobenzoyl, tetrahydropyranyl, 1-methoxycyclohexyl, ethoxycarbonyl, t-butoxycarbonyl, t-amyloxycarbonyl, benzyloxycarbonyl, p-methoxybenzyloxycarbonyl, p-ethoxybenzyloxycarbonyl or p-chlorobenzyloxycarbonyl, with a sulfonylating compound of the formula:

wherein R$_5$ represents methyl, ethyl, propyl, butyl, benzyl, p-toluyl, o-nitrophenyl, p-nitrophenyl or 2-naphthyl and X represents chlorine or bromine or —OSO$_2$R$_5$ group, to produce a sulfonyl compound of the formula:

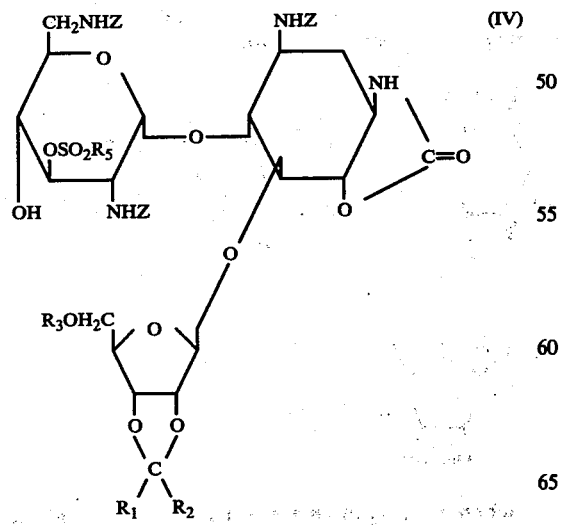

wherein Z, R$_1$, R$_2$, R$_3$ and R$_5$ are as defined above;

treating said sulfonyl compound under alkaline conditions to split the 1,6-carbamate linkage, whereby there is produced a compound of the formula:

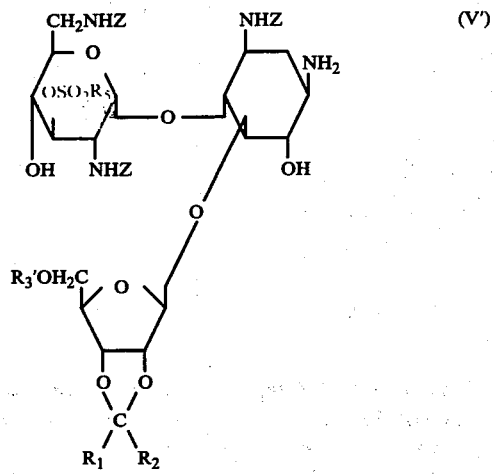

wherein Z, R$_1$, R$_2$ and R$_5$ are as defined above and R$_3'$ represents hydrogen or has the same meaning as R$_3$;

interacting the compound of the formula (V') with an acylating compound of the formula:

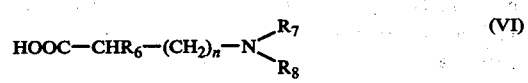

or

wherein R$_6$ represents —OH, n is an integer of 1 to 4, R$_7$ and R$_8$ each represents hydrogen or an acyl, alkyloxycarbonyl, aralkyloxycarbonyl or aryloxycarbonyl group and R$_9$ represents hydrogen or an alkyl or aryl group, or with a functional derivative of the carboxylic acid compound, to acylate the 1-amino group of the compound (V');

reacting the acylation product with an appropriate halogenating compound to iodinate, chlorinate, or brominate the 3'-position of the acylation product, followed by the reduction of the 3'-halo group; and then removing the remaining amino- and hydroxyl- protecting groups from the resultant product.

4. A process for the preparation of a compound of the general formula (I) as defined in claim 1, which comprises the steps of:

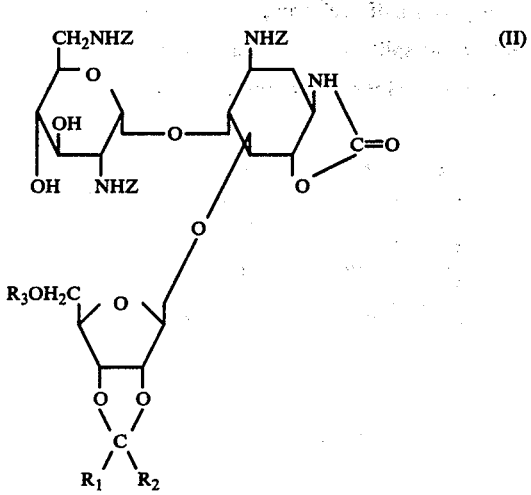

(II)

wherein each of Z represents an amino-protecting group of the formula —COOR$_4$ in which R$_4$ represents an alkyl, aryl or aralkyl group, R$_1$ and R$_2$ which may be the same or different, each represents hydrogen or an alkyl or aryl group or R$_1$ and R$_2$ taken together with the adjacent carbon atom form a cycloalkylidene or tetrahydropyranyl group and R$_3$ represents acetyl, propionyl, butyryl, benzoyl, para-chlorobenzoyl, p-nitrobenzoyl, tetrahydropyranyl, 1-methoxycyclohexyl, ethoxycarbonyl, t-butoxycarbonyl, t-amyloxycarbonyl, benzyloxycarbonyl, p-methoxybenzyloxycarbonyl, p-ethoxybenzyloxycarbonyl or p-chlorobenzyloxycarbonyl, with a sulfonylating compound of the formula:

$$R_5SO_2X \quad (III)$$

wherein R$_5$ represents methyl, ethyl, propyl, butyl, benzyl, p-toluyl, o-nitrophenyl, p-nitrophenyl or 2-naphthyl and X represents chlorine or bromine or —OSO$_2$R$_5$ group, to produce a sulfonyl compound of the formula:

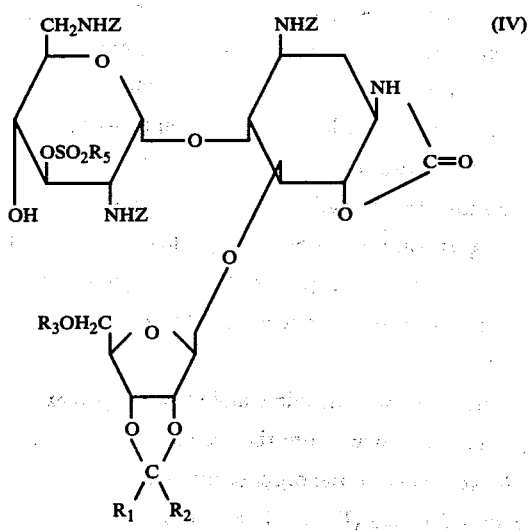

(IV)

wherein Z, R$_1$, R$_2$, R$_3$ and R$_5$ are as defined above;

treating said sulfonyl compound under alkaline conditions to split the 1,6-carbamate linkage, whereby there is produced a compound of the formula:

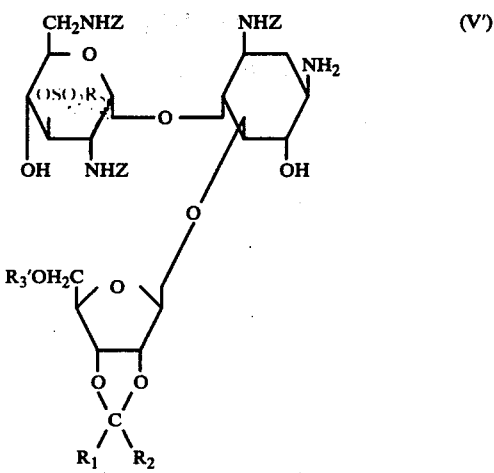

(V')

wherein Z, R$_1$, R$_2$ and R$_5$ are as defined above and R$_3$' represents hydrogen or has the same meaning as R$_3$;

interacting the compound of the formula (V') with an acylating compound of the formula:

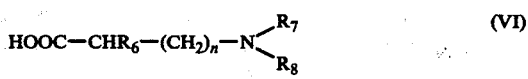

(VI)

or $$HOOC-CHR_6-(CH_2)_n-N=CHR_9 \quad (VII)$$

wherein R$_6$ represents —OH, $n$ is an integer of 1 to 4, R$_7$ and R$_8$ each represents hydrogen or an acyl, alkyloxy carbonyl, aralkyloxycarbonyl or aryloxycarbonyl group and R$_9$ represents hydrogen or an alkyl or aryl group, or with a functional derivative of the carboxylic acid compound, to acylate the 1-amino group of the compound (V');

reacting the acylation product with an appropriate halogenating compound to iodinate, chlorinate, or brominate the 3'-position of the acylation product;

removing the remaining amino- and hydroxyl-protecting groups from the halogenated compound to produce a compound of the formula:

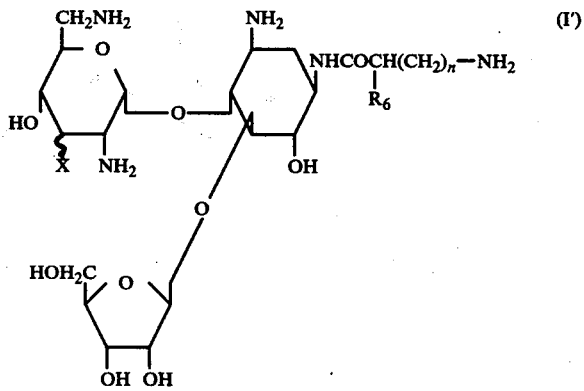

(I')

wherein X, R$_6$ and $n$ are as defined above; and then eliminating the 3'-halo group X from the compound of the formula (I') by the reduction thereof.

5. A process according to claim 1 in which the sulfonylation is carried out in a solvent of anhydrous pyridine.

6. A process according to claim 1 in which the reduction of the halogenated compound is carried out with the aid of a base selected from triethylamine and potassium hydroxide.

7. A process according to claim 1 in which the acylation is carried out in a mixed solvent of water and tetrahydrofuran.

* * * * *